United States Patent [19]

Pearson et al.

[11] Patent Number: 4,605,433

[45] Date of Patent: Aug. 12, 1986

[54] 1,2,4-TRIAZOLO[1,5-A]-1,3,5-TRIAZINE-2-SULFONAMIDES AND COMPOSITIONS AND METHODS OF CONTROLLING UNDESIRED VEGETATION

[75] Inventors: Norman R. Pearson, Walnut Creek; William A. Kleschick, Martinez, both of Calif.

[73] Assignee: The Dow Chemical Company, Midland, Mich.

[21] Appl. No.: 739,250

[22] Filed: May 30, 1985

[51] Int. Cl.$^4$ ................. C07D 251/72; C07D 487/04; A01N 43/64; A01N 43/90
[52] U.S. Cl. ........................................ 71/93; 71/90; 544/212
[58] Field of Search ...................... 544/212; 71/93, 90

[56] References Cited

U.S. PATENT DOCUMENTS

| 3,865,824 | 2/1975 | Kobe et al. | 544/212 |
| 3,910,907 | 10/1975 | O'Brien et al. | 544/212 |

FOREIGN PATENT DOCUMENTS

| 2720792 | 11/1977 | Fed. Rep. of Germany . | |
| 205905 | 1/1984 | German Democratic Rep. | 544/212 |

OTHER PUBLICATIONS

DeMilo et al., J. Het. Chem., vol. 10, pp. 231–233 (1973).

*Primary Examiner*—John M. Ford
*Attorney, Agent, or Firm*—Merlin B. Davey

[57] ABSTRACT

Novel compounds, e.g., 5,7-dimethyl-N-(2,6-dichlorophenyl)-1,2,4-triazolo[1,5a]-1,3,5-triazine-2-sulfonamide and their compositions and use in the control of weeds and in the suppression of nitrification of ammonium nitrogen in soil.

25 Claims, No Drawings

1,2,4-TRIAZOLO[1,5-A]-1,3,5-TRIAZINE-2-SULFONAMIDES AND COMPOSITIONS AND METHODS OF CONTROLLING UNDESIRED VEGETATION

BACKGROUND OF THE INVENTION

In recent years there has been a great deal of effort directed to the development of sulfonamides having herbicidal activity and several of these compounds have reached the stage of commercialization, i.e., chlorosulfuron and sulfometuron methyl. These compounds exhibit both preemergence and postemergence activity against undesirable vegetation and, in addition, have a low toxicity to mammals. The compounds of the prior art may be depicted as follows:

wherein Ar is usually a benzene derivative and Ar' is usually a pyrimidine or symmetrical triazine derivative.

In addition, there are a number of other sulfonamide herbicides that have been commercialized, for example, methyl sulfanilylcarbamate; 0,0-diisopropyl phosphorodithioate-S-ester with N-(2-mercaptoethyl)benzenesulfonamide; 3-isopropyl-1H-2,1,3-benzothiadiazin4(3H)-one 2,2-dioxide; N-[2,4-dimethyl-5-[[(trifluoromethyl)sulfonyl]amino]phenyl]acetamide; 3,5-dinitro-$N^4$, $N^4$-dipropylsulfanilamide and 2-t-butyl-4-(2,4-dichloro-5-isopropoxyphenyl)-$\Delta^2$-1,3,4-oxadiazolin-5-one.

SUMMARY OF THE INVENTION

We have now found that compounds having the formula:

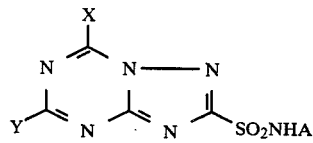

wherein Ar represents an aromatic (substituted or unsubstituted) or heteroaromatic (substituted or unsubstituted) ring system are herbicides and are active in the suppression of nitrification of ammonium nitrogen in soil and are effective in beneficially regulating the growth of crops.

DETAILED DESCRIPTION OF THE INVENTION

The aromatic or heteroaromatic ring systems include, for example, phenyl; 1- or 2-napthyl; 2-, 3- or 4-pyridyl; 2- or 3-thienyl; 2- or 3-furyl; 2-, 4- or 5-thiazolyl; 2-, 4- or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidiazolyl and 1-benztriazolyl. Typical examples of substituents found on the aromatic or heteroaromatic ring systems may be one, more than one or a combination of the following: halo (F, Cl, Br, I), alkyl, haloalkyl, aryl, hydroxy, alkoxy, haloalkoxy, aryloxy, substituted aryloxy, heteroaryloxy, substituted heteroaryloxy, amino, alkylamino, dialkylamino, nitro, alkylthio, haloalkylthio, alkylsulfinyl, haloalkylsulfinyl, alkylsulfonyl, haloalkylsulfonyl, substituted or unsubstituted arylthio, substituted or unsubstituted arylsulfinyl, substituted or unsubstituted arylsulfonyl, cyano, carboxylic acids (and derivatives of carboxylic acids such as esters derived from readily available alcohols and amides derived from ammonia or readily available primary and secondary amines), sulfonic acids (and derivatives of sulfonic acids such as sulfonates derived from readily available alcohols and sulfonamides derived from ammonia or readily available primary or secondary amines), formyl, alkylcarbonyl, haloalkylcarbonyl, arylcarbonyl, substituted arylcarbonyl, oximino, oxime ethers, carbinols (and carbinol derivatives such as ethers and esters derived from readily available alkylating agents and carboxylic acids respectively) and mercaptoalkyl (and derivatives of mercaptoalkyl groups such as thioethers and thioesters derived from readily available alkylating agents and carboxylic acids respectively).

The substituents on the triazolotriazine fragment of structure I are represented by X and Y. Substituents X and Y may be H, alkyl, haloalkyl, hydroxy, alkoxy, haloalkoxy, aryl, substituted aryl, halo (F, Cl, Br, I), alkylthio, arylthio, amino (including alkyl or aryl substituted amino), carboxylic acids and esters.

Preferred compounds of the invention have the general formula:

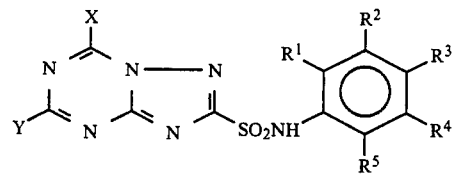

wherein $R^1$ represents halo (F, Cl, Br, I), —$NO_2$, phenyl, OAr, —$CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2H$, —$SO_2CF_2CCl_2H$, —$SR^6$, —$SOR^6$, —$SO_2R^6$, —CN, —$COOR^7$, —$CONH_2$, —$CONHR^8$, —$CONR^8(R^9)$, —$SO_3R^8$ and —$SO_3CH_2CF_3$; $R^2$ and $R^4$ represent H, halo (F, Cl, Br,I), $C_1$-$C_4$ alkyl, $COOR^7$ and —$OR^8$; $R^3$ is H; and $R^5$ represents H, $C_1$ to $C_4$ alkyl, halo (F, Cl, Br, I), $NO_2$, $CF_3$, —$OCF_3$, —$OCF_2CF_2H$, —$OCF_2CCl_2H$, —$OCH_2CF_3$, —$SCF_3$, —$SCF_2CF_2H$, —$SCF_2CCl_2H$, —$SOCF_3$, —$SOCF_2CF_2H$, —$SOCF_2CCl_2H$, —$SO_2CF_3$, —$SO_2CF_2CF_2H$, —$SO_2CF_2CCl_2H$, —$SR^6$, —$SOR^6$,—$SO_2R^6$, —CN, —COOR, —$CONH_2$, —$CONHR^8$, —$CONR^8(R^9)$, —$SO_3R^8$, —$SO_3CH_2CF_3$, —$CR^6R^6OR^6$ and —$CR^6R^6SR^6$ wherein Ar represents substituted or unsubstituted aryl or substituted or unsubstituted heteroaryl, $R^6$ represents H, aryl or $C_1$-$C_4$ alkyl, $R^7$ represents $C_1$-$C_6$ alkyl, alkenyl,alkynyl, aryl, substituted alkyl or substituted aryl and $R^8$ and $R^9$ individually represent $C_1$-$C_4$ alkyl; and X and Y represent H, $C_1$-$C_4$ alkyl, $C_1$-$C_4$ alkoxy, or halo (F, Cl, Br, I).

Preferred compounds of the invention also have the general formula:

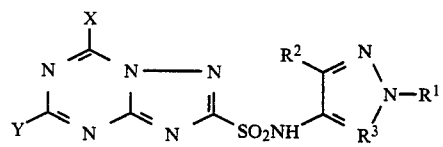

wherein $R^1$ represents H, alkyl or aryl, $R^2$ and $R^3$ represent independently H, $C_1$–$C_4$ alkyl, halo (F, Cl, Br, I), —$NO_2$, phenyl, —$CF_3$, benzyl, —$COOR^4$, —$CONH_2$, —$CONHR^5$, —$CONR^5R^6$, and CN wherein $R^4$ represents $C_1$–$C_6$ alkyl, alkenyl, alkynyl, arylalkyl, substituted alkyl or substituted aryl, $R^5$ and $R^6$ individually represent $C_1$–$C_4$ alkyl; and X and Y represent H, $C_1$–$C_4$ alkyl, $C_1$–$C_4$ alkoxy, or halo (F, Cl, Br, I).

The synthesis of compounds of general structure I can be carried out as illustrated in Scheme I. Reaction of sulfonyl chloride IV with the appropriate aromatic (substituted or unsubstituted) or heteroaromatic (substituted or unsubstituted) amino compound ($ArNH_2$) under basic conditions yields the desired product I. A wide range of solvents may be employed (i.e., $CH_2Cl_2$, $CH_3CN$ or pyridine) at temperatures ranging from 0° C. to reflux. Bases which serve as catalysts include pyridine, 4-dimethylaminopyridine and tertiary alkylamines such as triethylamine or N-methylmorpholine. In addition it is sometimes advantageous to use a combination of pyridine derived base catalysts and tertiary amine bases. The use of pyridine as a solvent is convenient as the pyridine can serve both as a solvent and catalyst in the transformation.

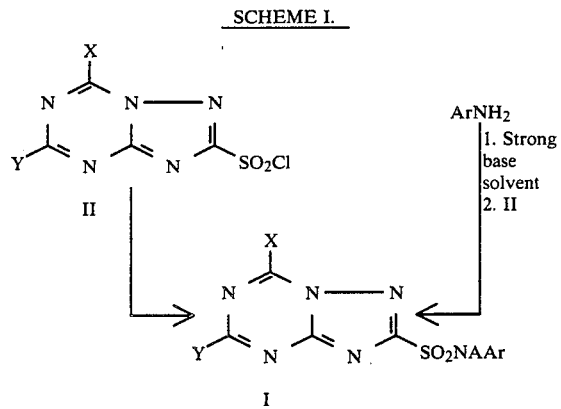

SCHEME I.

An additional alternative route to compounds of general formula I is illustrated in Scheme I. In cases where the amino compound ($ArNH_2$) is less reactive (less nucleophic) is it advantageous to prepare a metal derivative of the amino compound by treatment with a strong base. The corresponding amide bases are generally prepared in ether solvents (i.e., THF) using strong bases such as alkali metal alkyls (i.e., n-BuLi) or alkali metal hydrides (i.e., NaH or KH) at temperatures ranging from —80° C. to 0° C. The amide thus generated in situ can be reacted with sulfonylchloride IV to yield the desired product I. Generally, molar ratios of the starting amino compound to sulfonyl chloride of 2 to 3 are used to ensure complete reaction.

Sulfonyl chlorides II are new and represent key intermediates in the synthesis of sulfonamides I. Sulfonyl chlorides II may be prepared according to routes outlined in Scheme II. Mercaptan III may be converted to sulfonyl chloride II by treatment with $Cl_2$ in an aqueous acidic medium. Generally the medium would be aqueous acetic acid or aqueous HCl. The temperature of the reaction mixture is generally maintained between —20° C. and 25° C. during the course of the chlorine addition. Most preferably, temperature ranges between —20° C. and 0° C. are employed to minimize unwanted side reactions such as hydrolysis of II to the corresponding sulfonic acid. Alternatively, the mercaptan III may be suspended in a two phase system of aqueous acid (i.e., HCl) and an organic solvent (i.e., $CH_2Cl_2$) and treated with sodium hypochlorite. This serves to convert III to the sulfonyl chloride II. The solubility of the product in the organic phase serves to protect it from hydrolysis to the sulfonic acid. Again, temperatures in the range of —20° C. to 25° C. are employed with temperatures in the range of —5° C. to 5° C. being most generally used.

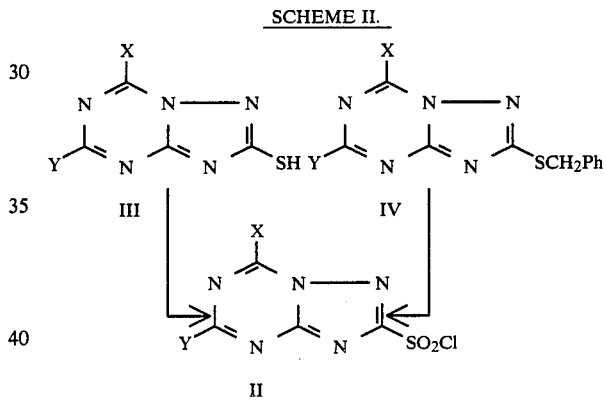

SCHEME II.

As an alternative, it is sometimes preferred to prepare sulfonyl chloride II from benzyl sulfide IV (Scheme II). Reaction conditions as described above for the conversion of III to II are operable. This procedure yields by-products containing benzyl residues which are generally removed by washing the product with water and/or an appropriate organic solvent and drying in vacuo.

Compounds of general structure III or IV may be prepared as illustrated in Scheme III. The triazine may be constructed in two steps (Path A) by treatment of the appropriate aminotriazole V (R=H, $PhCH_2$) with an imidate ester followed by an orthoester, or in one step (Path B) using reagents of structure VI. Analogous procedures have been described in the literature for preparing fused triazines starting with 3-amino pyrazoles (J. Het. Chem., 12, 1255 (1975) and J. Het. Chem., 22, 7 (1985)). This constitutes the first application of this methodology to the synthesis of 1,2,4-triazolo[1,5-2]-1,3,5-triazines.

SCHEME III.

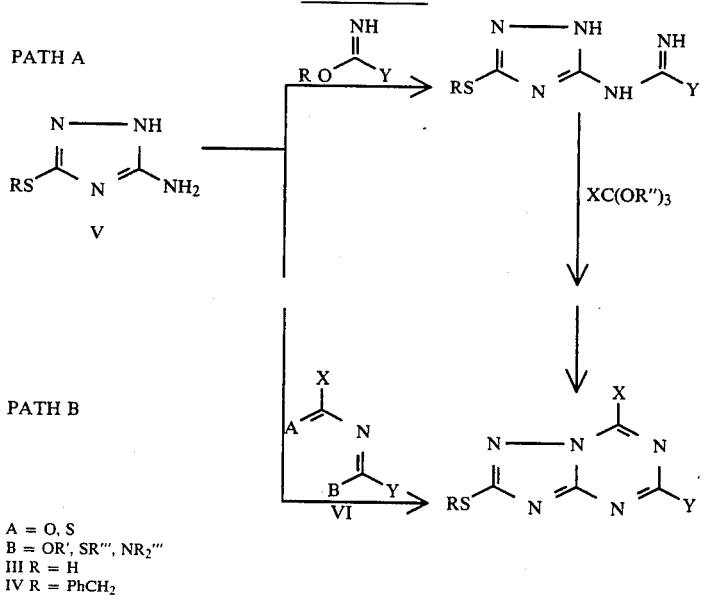

A = O, S
B = OR', SR''', NR₂'''
III R = H
IV R = PhCH₂

In addition, the triazolotriazine sulfonamides may be prepared by condensation of aminotriazole VII with reagents VI as shwon in Scheme IV.

SCHEME IV.

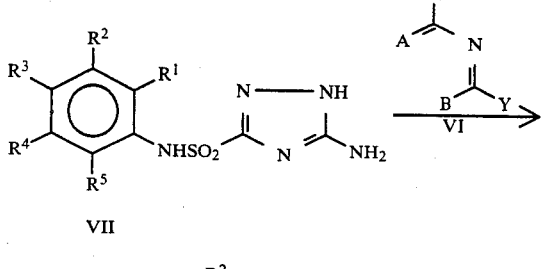

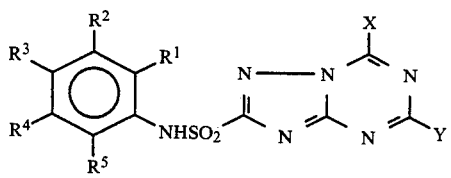

The majority of the amino compounds (ArNH₂) utilized to prepare the compounds of the present invention (see structure I) as illustrated in Scheme I were obtained from commerical sources or prepared by known literature procedures or minor modifications of literature procedures.

A number of the amino compounds (ArNH₂) used to prepare the compounds of the present invention are derivatives of anthranilic acid. Many of these compounds can be prepared according to conventional methods described by S. J. Holt et al., *Royal Soc. Proc, Sec. B,* 148, 481 (1958), P.W. Sadler et al., *J. Am. Chem. Soc.,* 78, 1251 (1956), and G. Reissenweber et al., U.S. Pat. No. 4,310,677 (1982). Other anthanilic acid derivatives can be prepared by standard derivatizations (i.e., conversion to esters and amides) of known substituted or unsubstituted 2-nitrobenzoic acids followed by reduction of the nitro group as represented in Scheme V.

SCHEME V.

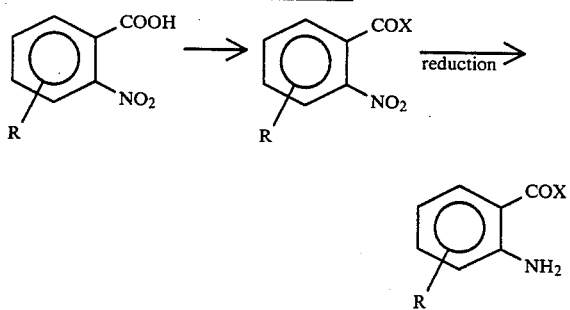

X = alkoxy, amino or alkylamino

A number of the amino compounds are prepared by reduction of anthranilic acids or esters and subsequent derivatization of the reduction product. This is outlined in Scheme VI. The carbinol reduction products may be derivatized by reaction with base and various electrophiles (i.e., alkyl halides and carboyxlic acid chlorides).

SCHEME VI.

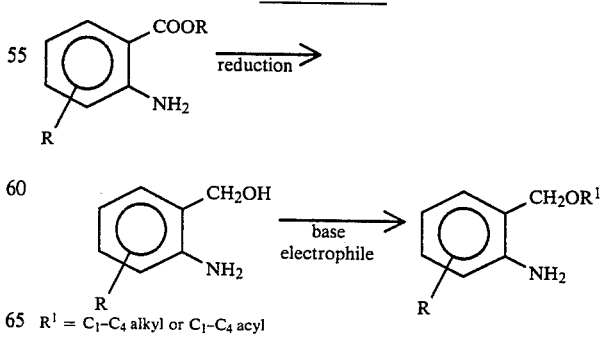

R¹ = C₁-C₄ alkyl or C₁-C₄ acyl

A large number of the amino compounds utilized in the preparation of the compounds of this invention contain halogen substituents ortho to the amino group. Many of these compounds were prepared by halogenation of the corresponding material bearing no substituent in the ortho position according to a general procedure described by R. S. Neale et al., *J. Org. Chem.*, 29, 3390 (1964). The starting materials for these halogenations were commercially available or known in the literature (i.e., British Pat. No. 695,164 (1953); D. S. Noyce et al., *J. Org. Chem.* 26, 1732 (1961) and U.S. Pat. No. 3,813,234 (1974)). In certain instances to facilitate the transformation and insure ortho selectivity in the halogenation process the starting materials for the halogenation were acetamide derivatives (ArNHCOCH$_3$) or derivatives containing groups (i.e., Br) which would block halogenation at other positions in the molecule (i.e., para to the amino group). Following halogenation the acetamide derivatives were hydrolized back to the desired amino compound and the blocking groups were removed (i.e., Br in the para position was selectively removed by reduction in the presence of —Cl in the ortho position). Other chlorine and bromine substituted amino compounds were prepared by known procedures (i.e., U.S. Pat. No. 4,188,342 (1980); C. R. Rasmussen et al. *J. Med. Chem.*, 21, 1044 (1978); H. E. Dadswell et al. *J. Chem. Soc.*, 1102 (1927); U.S. Pat. No. 3,813,234 (1974) and P. B. D. DeLaMare and J. H. Ridd, "Aromatic Substitution, Nitration and Halogenation", Academic Press, New York (1959), p. 106.

A number of the amino compounds used as starting materials for the compounds of this invention contain sulfur substituents in the ortho position. These were prepared using known procedures (i.e., R. R. Gupta et al., *Heterocycles*, 16, 1527 (1981)). In some cases alkylthio groups were present and these were synthesized by alkylation of the corresponding mercaptan. Compounds having alkyl or aryl sulfinyl or sulfonyl groups were synthesized by oxidation of the appropriate alkyl or arylthio groups.

Some starting amino compounds containing amino, alkylamino, aryloxy or pyridyloxy groups were prepared by catalytic reduction of the corresponding nitro compounds. The amino, alkylamino, aryloxy or pyridyloxy group were usually introduced via displacement of a leaving group ortho to the nitro group in the requisite nitrobenzene.

Other starting amino compounds were prepared by procedures involving metalation of the aromatic ring of N-substituted derivatives (i.e., t-butoxycarbonyl derivatives) of an aromatic amino compound followed by the resulting organometallic reagent with an electrophile. This general procedure is described in H. Gschwend, *Org. Reactions*, Vol. 20, 1–360 (1979) and is outlined in Scheme VII. Suitable metalating agents are organolithium reagents (i.e., n-butyllithium or t-butyllithium). Typical electrophiles include alkyl halides (i.e., methyl iodide, ethyl iodide), aldehydes (i.e., formaldehyde, acetaldehyde), ketones (i.e., acetone), alkyl or aryl sulfonyl halides (i.e., methyl sulfonyl chloride), and dialkyl or diaryldisulfides (i.e., dimethyldisulfide). These electrophiles are useful for the introduction of alkyl, hydroxy alkyl and arylthio or arylthio groups to the position ortho to the amino group. After the reaction of the organometallic intermediate with the electrophile the nitrogen substituent is removed by hydrolysis.

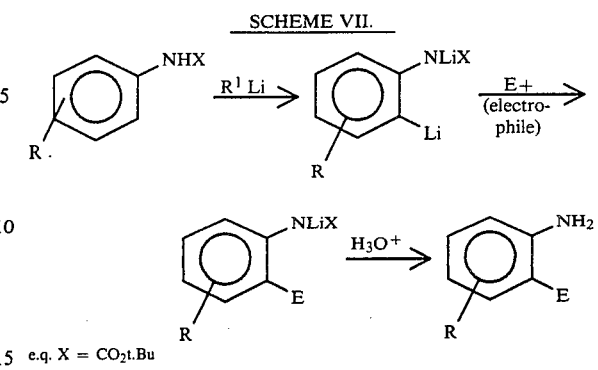

e.q. X = CO$_2$t.Bu

Other aromatic amino compounds used to prepare compounds of the present invention are prepared by conversion of carboxylic acid groups or derivatives of carboxylic acid groups to amino groups by standard methodology. Such a transformation is illustrated in Scheme VIII and described in *J. Royal. Netherlands Chem. Soc.*, 97, 53 (1978).

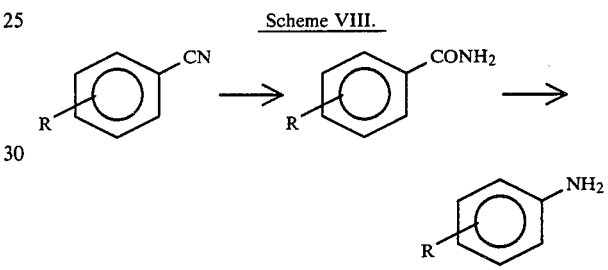

Other amino compounds such as those which are heteroaromatic amino compounds are prepared by known procedures such as those described in *Rec. Trav. Chim.*, 69, 673 (1950), T. Talik et al., *Chem. Abstracts*, 59: 8698a (1963) and L. C. Behr and R. Fusco In "*Heterocyclic Compounds*", A. Weissberger, Ed. Vol 22, Interscience Publishers, New York (1967), p 3–174 or straightforward modification of the art described above.

The compounds of the present invention are effective herbicides. They have utility for broadspectrum pre- and/or postemergence weed control in areas where complete vegetation control is desired. The subject compounds are also useful for selective pre- and/or postemergence weed control in agricultural crops.

For all such uses, unmodified active ingredients of the present invention can be employed. However, the present invention embraces the use of a herbicidally-effective amount of the active ingredients in composition form with an inert material known in the art as an agricultural adjuvant or carrier in solid or liquid form. Such adjuvants or carriers must not be phytotoxic to valuable crops particularly at the concentration employed in applying the composition in attempting selective weed control in the presence of crops. If weed control is desired in the absence of crops, it is generally sufficient to employ adjuvants or carriers which do not leave a persistent phytotoxic residue.

Thus, for example, an active ingredient can be dispersed on a finely-divided solid and employed therein as a dust. Also, the active ingredients, as liquid concentrates or solid compositions comprising one or more of the active ingredients can be dispersed in water, typically with aid of a wetting agent, and the resulting aqueous dispersion employed as a spray. In other procedures the active ingredients can be employed as a constituent of organic liquid compositions, oil-in-water and water-in-oil emulsions or dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

Organic solvents that can be employed include toluene, xylene, kerosene, diesel fuel, fuel oil, and petroleum naphtha, ketones such as acetone, methylethyl ketone and cyclohexanone, chlorinated hydrocarbons such as trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butylcarbitol acetate and glycerine. Mixtures of water and organic solvents, either as emulsions or solutions, can be employed.

The active ingredients of the present invention can also be applied as aerosols, e.g., by dispersing them by means of a compressed gas such as one of the fluorocarbons or one of its hydrocarbon successors.

The active ingredients of the present invention can also be applied with solid adjuvants or carriers such as talc, pyrophyllite, synthetic fine silica, attapulgus clay, kieselguhr, chalk, diatomaceous earth, lime, calcium carbonate, bentonite, Fuller's earth, cotton seed hulls, wheat flour, soybean flour, pumice, tripoli, wood flour, walnut shell flour, redwood flour and lignin.

As stated, it is frequently desirable to incorporate a surface-active agent in the compositions of the present invention. Such surface-active or wetting agents are advantageously employed in both the solid and liquid compositions. The surface-active agent can be anionic, cationic or nonionic in character.

Typical classes of surface-active agents include alkyl sulfonate salts, alkylaryl sulfonate salts, alkylaryl polyether alcohols, fatty acid esters of polyhydric alcohols and the alkylene oxide addition products of such esters, and addition products of long-chain mercaptans and alkylene oxides. Typical examples of such surface-active agents include the sodium alkylbenzene sulfonates having 10 to 18 carbon atoms in the alkyl group, alkyl phenol ethylene oxide condensation products, e.g., p-isooctylphenol condensed with 20 ethylene oxide units, soaps, e.g., sodium stearate and potassium oleate, sodium salt of propylnaphthalene sulfonic acid, di(2-ethylhexyl)ester of sodium sulfosuccinic acid, sodium lauryl sulfate, sodium decyl sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g., Ethofat 7 and 13, sodium N-methyl-N-oleyl taurate, sodium dibutylnaphthalene sulfonate, sodium lignin sulfonate, polyethylene glycol stearate, sodium dodecyl benzene sulfonate, tertiary dodecyl polyethylene glycol thioether (nonionic 218), long-chain ethylene oxide-propylene oxide condensation products e.g., Pluronic 61 (molecular weight about 1000), polyethylene glycol ester of tall oil acids, sodium octophenoxyethoxyethyl sulfate, tris(polyoxyethylene)-sorbitan monostearate (Tween 60), and sodium dihexylsulfosuccinate.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent, preferably 15–50 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application. In such embodiments, the pesticidal compound is employed as a supplemental toxicant for the same or for a different pesticidal use or as an additament.

The compounds of the present invention are particularly useful in combination with other herbicides including the substituted urea herbicides such as 3-(3,4-dichlorophenyl)-1,1-dimethylurea, 3-(3,4-dichlorophenyl)-1-methoxy-1-methylurea (Lorox®) and 1,1-dimethyl-3-(α, α, α-trifluoro-m-tolyl)urea (Cotoran®); the triazines such as 2-chloro-4-(ethylamino)-6-(isopropylamino)-s-triazine and 2-chloro-4-(1-cyano-1-methylethylamino)-6-ethylamino-s-triazine (Bladex®); the uracils such as 5-bromo-3-sec-butyl-6-methyluracil; N-(phosphonomethyl)glycine; the phenoxys such as 2,4-dichlorophenoxyacetic acid; picolinic acids such as 4-amino-3,5,6-trichloropicolinic acid (Tordon®) and 3,6-dichloropicolinic acid (Lontrel®); 4-chloro-2-butynyl-3-chlorophenyl carbamate (Carbyne®); diisopropylthiocarbamic acid, ester with 2,3-dichloroallyl alcohol (Avadex®); diisopropylthiocarbamic acid, ester with 2,3,3-trichloroallyl alcohol (Avadex® BVD); ethyl-N-benzoyl-N-(3,4-dichlorophenyl)-2-aminopropionate (Suffix®); 1,2-dimethyl-3,5-diphenylpyrazolium methylsulfate (Avenge®); methyl (2-[4-(2,4-dichlorophenoxy)-phenoxy]propanoate) (Hoelon®); butyl 2-[4-[(5-(trifluoromethyl)-2-pyridinyl)oxy]phenoxy]propanoate (Fusilade®); esters of 2-[4-[(3-chloro-5-trifluoromethyl)-2-pyridinyl)-oxy]phenoxy]propionic acid; 4-amino-6-tert-butyl-3-(methylthio)-1,2,4-triazin-5-(4H)-one (Lexone®); 3-isopropyl-1H-2,1,3-benzothiadiazin-(4)-3H-one 2,2-dioxide; α, α, α-trifluoro-2,6-dinitro-N,N-dipropyl-p-toluidine; 1,1'-dimethyl-4,4'-bipyridinium ion; 2-chloro-2',6'-diethyl-(methoxymethyl)acetanilide; and 2-[1-(ethoxyimino)-butyl]-5-[(2-ethylthio)propyl]-3-hydroxy-2-cyclohexen-1-one (Poast®).

The rates of application for compounds of the invention are determined by a number of factors including the active ingredient being applied, the particular action desired (e.g., general or selective control), the plant species to be modified and the stage of growth thereof, the part of the plant to be contacted with the toxic active ingredient, the formulation selected, weather and climate, etc. Thus, it is to be understood that all of the active ingredients of the present invention and compositions containing the same may not be equally effective at similar concentrations or against the same plant species.

It has further been found that soil nitrogen may be conserved and plant nutrition improved by treating plant growth media with the novel compounds of this invention.

By the practice of the embodiment of the invention, the nitrification of ammonium nitrogen in the soil to nitrate nitrogen is suppressed, thereby preventing the rapid loss of ammonium nitrogen from the soil. Furthermore, by proper distribution of the novel compounds, this action of inhibiting the transformation of ammonium nitrogen to nitrate nitrogen is effective over a prolonged period of time including those situations where treated fertilizer is stored for some time before use. The ammonium nitrogen may arise from added ammonium nitrogen fertilizers or be formed in the soil by conversion of the organic nitrogen constituents found in soil or added thereto as components of organic fertilizers.

The provision of an effective but sublethal dosage of the active ingredient in the soil or growth medium is essential for the practice of the present invention. The preferred amounts to be employed are dependent upon the particular situation. Thus, in determining the amount to be employed, consideration is made not only of the treatment need, i.e., soil pH, temperature, soil type, etc., but also of the mode of application to the soil. When the active ingredient is to be applied in a broadcast application, the concentration may frequently be less than in row or band application where for a substantial depth and width within the vicinity of application there may be a very high concentration of the active ingredient. When application is made near the root zone of growing plants or when application is made immediately prior to seeding or transplanting, the amounts supplied are frequently at a lower rate than when application is made at the end of the growing season to prepare the soil for the following season. By dispersing very large dosages in growth media, a prolonged inhibition of nitrification may be obtained over a period of many months. The concentration of the active ingredient is eventually reduced to a minimum by decomposition in the soil.

In one method for carrying out this embodiment of the invention, the active ingredient is distributed throughout the growth media in a broadcast application such as by spraying, dusting, distributing in irrigation water, etc. In such application, the active ingredient is supplied in amounts sufficient to permeate the growing area of soil. In field administration, the active ingredient may be distributed through such cross-section of the soil as to provide for the presence therein of an effective concentration of the agent. It is usually preferred that the active ingredient be distributed to a depth of at least two inches (5.08 cm) below the soil surface.

In another method for carrying out the present invention, the active ingredient is administered to the growth medium in a band or row application. In such application, administration is made with or without carrier in an amount sufficient to supply to soil or growth medium a concentration of the active ingredient which may be as high as 4000 ppm or more. After administration with or without discing or dragging, subsequent irrigation or rainfall distributes the active ingredient throughout the growth medium.

In one embodiment of the present invention, the active ingredient is distributed throughout the growth media prior to seeding or transplanting the desired crop plant.

In another embodiment, the soil in the root zone of growing plants is treated with the active ingredient in an amount effective to inhibit nitrification. Oftentimes, it is desirable to treat the soil adjacent to plants, and this procedure may be carried out conveniently in sidedressing operations.

In a further embodiment, soil may be treated with the compounds following harvest or after fallowing to prevent rapid loss of ammonium nitrogen and to build up the ammonium nitrogen formed by conversion of organic nitrogen compounds. Such practice conserves the soil nitrogen for the following growing season. In such application, the upper limit is primarily an economic consideration.

In an additional embodiment, the soil is treated with the active ingredient in conjunction with the application of reduced nitrogen fertilizers. The treatment with the active ingredient may be carried out prior to, subsequent to or simultaneously with the application of fertilizers. Such practice prevents the rapid loss of the ammonium nitrogen added as fertilizer and of the ammonium nitrogen formed from organic nitrogen in fertilizers by the action of soil microorganisms. The administration to the soil of the active ingredient in an ammonium nitrogen or ammonium nitrogen forming fertilizer composition constitutes a preferred embodiment of the present invention.

The present invention may be carried out by distributing the active ingredient in an unmodified form through growth medium. The present method also embraces distributing the active ingredient as a constituent in liquid or finely divided solid compositions. In such practice, the active ingredient may be modified with one or more additaments or soil treating adjuvants including water, petroleum distillates or other liquid carriers, surface-active dispersing agents, finely divided inert solids and nitrogen fertilizers. Depending upon the concentration of the active ingredient, such augmented composition may be distributed in the soil without further modification or be considered a concentrate and subsequently diluted with additional inert carrier to produce the ultimate treating composition. The required amount of the active ingredient may be supplied to growth media in an organic solvent carrier, in an aqueous carrier or in a solid carrier. When an organic solvent carrier is employed, it may be further dispersed in an aqueous liquid carrier.

The concentration of the active ingredient in compositions to be employed for the treatment of growth media is not critical and may vary considerably provided the required dosage of effective agent is supplied to the growth media. The concentration of the active ingredient may vary from 0.00001 percent by weight to 95 percent by weight of the composition, depending on whether the composition is a treating composition or a concentrate composition and whether it is in the form of a solid or a liquid. In aqueous liquid treating compositions, concentrations of from about 0.00001 percent to about 0.25 percent by weight of the active ingredient is considered the preferred composition. The concentration of the active ingredient in organic solvents may be from about 2 to about 95 percent by weight. Concentrate liquid compositions generally contain from about 2.5 to about 95 percent by weight of the active ingredient. Treating compositions generally contain from about 0.0001 percent to about 10 percent by weight of the active ingredient while concentrate compositions contain from about 2.5 to about 95 percent.

Liquid compositions containing the desired amount of the active ingredient may be prepared by dispersing the latter in one or more liquid carriers such as water or an organic solvent, with or without the aid of a suitable surface-active dispersing agent or emulsifying agent. Suitable organic solvents include acetone, diisobutylketone, methanol, ethanol, isopropyl alcohol, toluene, methylene chloride, chlorobenzene and the petroleum distillates. The preferred organic solvents are those which are of such volatility that they leave little permanent residue in the soil. When the solutions of the active ingredient in organic solvents are to be further diluted to produce aqueous dispersions, the preferred solvents include acetone and the alcohols. When the liquid carrier is entirely organic in nature, particularly desirable carriers are the petroleum distillates boiling almost entirely under 400° F. (204° C.) at atmospheric pressure and having a flash point above 100° F. (38° C.). Dispersing and emulsifying agents which may be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from about 1 to about 20 percent by weight of the active ingredient.

Solid compositions containing the active ingredient may be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with the active ingredient or wet with a solution or dispersion thereof in a volatile organic solvent. Depending upon the proportions of ingredients, these compositions may be employed without further modification or be considered concentrates and subsequently further diluted with solid surface-active dispersing agent, talc, chalk, gypsum or the like to obtain the desired treating composition. Furthermore, such concentrate compositions have the properties of wettable powders and may be dispersed in water with or without added dispersing agent or agents to prepare aqueous soil treating compositions.

Soil treatment compositions may be prepared by dispersing the active ingredient in fertilizers such as ammonium fertilizer or organic nitrogen fertilizer. The resulting fertilizer composition may be employed as such or may be modified as by dilution with additional nitrogen fertilizer or with inert solid carrier to obtain a composition containing the desired amount of active agent for the treatment of soil. Further, an aqueous dispersion of the active ingredient-fertilizer composition may be prepared and administered to the growth medium. Fertilizer compositions comprising the active ingredient in intimate admixture with ammonium fertilizers constitute preferred embodiments of the present invention.

In fertilizer compositions comprising a reduced nitrogen fertilizer, it is desirable that the active ingredient be present in an amount of at least 0.05 percent by weight basedon the weight of the nitrogen present in the fertilizer as reduced nitrogen and may be present in amounts as high as 95 percent by weight of the reduced nitrogen in the fertilizer. Thus, when a fertilizer composition contains both reduced nitrogen and other forms of nitrogen such as in the case of ammonium nitrate fertilizer compositions, the amount of the active ingredient is based on the weight of nitrogen present in the ammonium component.

In operations carried out in accordance with the present invention, the soil may be treated in any convenient fashion with the active compound or a composition containing the latter. For example, these modified or unmodified compositions may be mechanically mixed with soil; applied to the surface of soil and thereafter dragged or disced into the soil to a desired depth; or transported into the soil with a liquid carrier such as by injection, spraying or irrigation. When the distribution is carried out by introducing the compound in the water employed to irrigate the soil, the amount of water is varied in accordance with the moisture content of the soil in order to obtain a distribution of the compound to the desired depth. The compound may be readily and conveniently distributed to a depth of a few inches to four feet by irrigation methods. The preferred methods embrace procedures using any of these steps or combination of steps wherein the compound is distributed in the soil substantially simultaneously with a reduced nitrogen fertilizer.

We claim:
1. A compound having the formula:

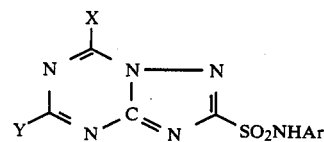

wherein X and Y independently represent hydroxy, carboxyl, hydrogen, $C_1$–$C_4$ alkyl, $C_1$–$C_4$ haloalkyl, $C_1$–$C_4$ alkoxy, $C_1$–$C_4$ haloalkoxy or halogen and Ar represents substituted or unsubstituted radicals which are phenyl; 1- or 2-naphthyl; 2-, 3- or 4-pyridyl; 2- or 3-thienyl; 2- or 3-furyl; 2-, 4- or 5-thiazolyl; 2-, 4-or 5-imidazolyl; 2-, 4- or 5-oxazolyl; 3-, 4- or 5-isothiazolyl; 3-, 4- or 5-isoxazolyl; 3-, 4- or 5-pyrazolyl; 2-benzthiazolyl; 2-benzoxazolyl; 2-benzimidazolyl or 1-benztriazolyl, wherein the substituents in the above radicals are halogen, —$NO_2$, $C_1$–$C_4$ haloalkyl, $C_1$–$C_4$ haloalkylsulfinyl, $C_1$–$C_4$ haloalkylthio, $C_1$–$C_4$ haloalkylsulfonyl, $C_1$–$C_4$ alkyl, cyano, —$CONH_2$, —$CONHR^8$, —$CONR^8R^9$, —$COOR^7$ and —$SO_3R^8$ wherein $R^7$, $R^8$ and $R^9$ represent $C_1$–$C_4$ alkyl.

2. Compound of claim 1 wherein Ar is phenyl, 1-naphthyl or 4-pyrazolyl.

3. Compound of claim 1 wherein Ar is

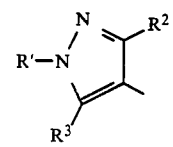

wherein $R^1$ is H, alkyl or phenyl and $R^2$ and $R^3$ independently represents H, halo, alkyl, haloalkyl, phenyl, substituted phenyl, hydroxy, alkoxy, haloalkyloxy, phenoxy, substituted phenoxy, amino, alkylamino, dialkylamino, nitro, alkylthio, haloalkylthio, alkylsulfinyl, haloalkylsulfinyl, alkylsulfonyl, haloalkylsulfonyl, substituted or unsubstituted phenylthio, substituted or unsubstituted phenylsulfinyl, substituted or unsubstituted phenylsulfonyl, cyano, carboyxlic acids, lower alkyl esters of carboxylic acids, amides or carboxylic acids derived from ammonia or lower alkyl primary or secondary amines, sulfonic acids, sulfonates derived from lower alcohols and sulfonamides derived from ammonia or lower alkyl mono or dialkylamines, formyl, alkylcarbonyl, haloalkylcarbonyl, phenyl carbonyl, substituted phenyl carbonyl, and mercaptoalkyl wherein the substituents are halogen, $-NO_2$, haloalkyl, haloalkylsulfinyl, haloalkylthio, haloalkylsulfonyl, alkyl, cyano, $-CONH_2$, $-CONHR^8$, $-CONR^8R^9$, $-COOR^7$ and $-SO_3R^8$ wherein $R^7$, $R^8$ and $R^9$ represent $C_1$-$C_4$ alkyl and wherein the alkyl, alkoxy, haloalkyl, haloalkoxy groups contain from 1 to 4 carbon atoms.

4. Composition comprising an inert carrier in admixture with an herbicidally effective amount of a compound or a salt of a compound of claim 1.

5. Composition comprising an inert carrier in admixture with an herbicidally effective amount of a compound or a salt of a compound of claim 1.

6. Composition comprising an inert carrier in admixture with an herbicidally effective amount of a compound or a salt of a compound of claim 2.

7. Composition comprising an inert carrier in admixture with an herbicidally effective amount of a compound or a salt of a compound of claim 1.

8. Composition comprising an inert carrier in admixture with an herbicidally effective amount of a compound or a salt of a compound of claim 3.

9. Composition comprising an inert carrier in admixture with an herbicidally effective amount of a compound or a salt of a compound of claim 1.

10. Method of controlling undesired vegetation which comprises the application to the locus of said vegetation of an herbicidally effective amount of a compound of claim 1.

11. Method of controlling undesired vegetation which comprises the application to the locus of said vegetation of an herbicidally effective amount of a compound of claim 1.

12. Method of controlling undesired vegetation which comprises the application to the locus of said vegetation of an herbicidally effective amount of a compound of claim 2.

13. Method of controlling undesired vegetation which comprises the application to the locus of said vegetation of an herbicidally effective amount of a compound of claim 1.

14. Method of controlling undesired vegetation which comprises the application to the locus of said vegetation of an herbicidally effective amount of a compound of claim 3.

15. Method of controlling undesired vegetation which comprises the application to the locus of said vegetation of an herbicidally effective amount of a compound of claim 1.

16. A compound having the formula

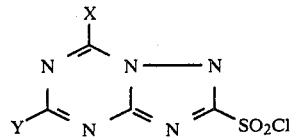

wherein X and Y independently represent hydrogen, $C_1$-$C_4$ alkyl, $C_1$-$C_4$ haloalkyl, $C_1$-$C_4$ alkoxy, $C_1$-$C_4$ haloalkoxy, halogen, phenyl or substituted phenyl wherein the substituents are halogen, $-NO_2$, $C_1$-$C_4$ haloalkyl, $C_1$-$C_4$ haloalkylsulfinyl, $C_1$-$C_4$ haloalkythio, $C_1$-$C_4$ haloalkylsulfonyl, $C_1$-$C_4$ alkyl, cyano, $-CONH_2$, $-CONHR^8$, $-CONR^8R^9$, $-COOR^7$ and $-SO_3R^8$ wherein $R^7$, $R^8$ and $R^9$ represent $C_1$-$C_4$ alkyl.

17. A compound having the formula

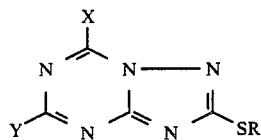

wherein X and Y independently represent hydrogen, $C_1$-$C_4$ alkyl, $C_1$-$C_4$ haloalkyl, $C_1$-$C_4$ alkoxy, $C_1$-$C_4$ haloalkoxy, halogen, phenyl or substituted phenyl wherein the substituents are halogen, $-NO_2$, $C_1$-$C_4$ haloalkyl, $C_1$-$C_4$ haloalkylsulfinyl, $C_1$-$C_4$ haloalkylthio, $C_1$-$C_4$ haloalkylsulfonyl, alkylsulfonyl, $C_1$-$C_4$ alkyl, cyano, $-CONH_2$, $-CONHR^8$, $-CONR^8R^9$, $-COOR^7$ and $-SO_3R^8$ wherein $R^7$, $R^8$ and $R^9$ represent $C_1$-$C_4$ alkyl.

18. Compound of claim 17 wherein X and Y independently represent hydrogen, halo, $C_1$-$C_4$ alkyl or $C_1$-$C_4$ alkoxy, and R represents H or benzyl.

19. Compound of claim 17 wherein X and Y are methyl, and R is hydrogen.

20. Compound of claim 17 wherein X and Y are methyl, and R is benzyl.

21. Compound of claim 17 wherein X is methyl, and Y and R are hydrogen.

22. Compound of claim 17 wherein X is methyl, Y is hydrogen, and R is benzyl.

23. Compound of claim 17 wherein Y is methyl, and X and R are hydrogen.

24. Compound of claim 17 wherein Y is methyl, X is hydrogen and R is benzyl.

25. Compound of claim 17 wherein X and Y are hydrogen, and R is benzyl.

* * * * *

UNITED STATES PATENT AND TRADEMARK OFFICE
CERTIFICATE OF CORRECTION

PATENT NO. : 4,605,433     Page 1 of 8
DATED     : August 12, 1986
INVENTOR(S) : Norman R. Pearson and William A. Kleschick It is certified that error appears in the above-identified patent and that said Letters Patent is hereby corrected as shown below:

Column 2, line 40, "-SO$_2$CF$_2$H," should read -- -SO$_2$CF$_2$CF$_2$H,--.

Column 2, line 50, "-COOR," should read -- -COOR$^7$,--.

Column 5 and 6, formula SCHEME III, between lines 1 and 23,

"

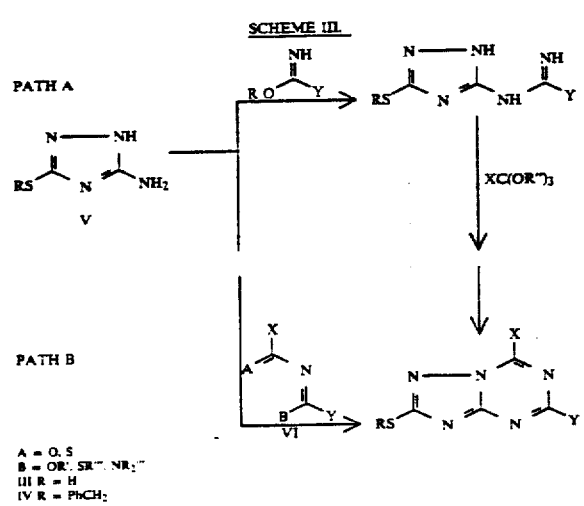

should read

UNITED STATES PATENT AND TRADEMARK OFFICE
CERTIFICATE OF CORRECTION

PATENT NO. : 4,605,433

DATED : August 12, 1986

INVENTOR(S) : Norman R. Pearson and William A. Kleschick

It is certified that error appears in the above-identified patent and that said Letters Patent is hereby corrected as shown below:

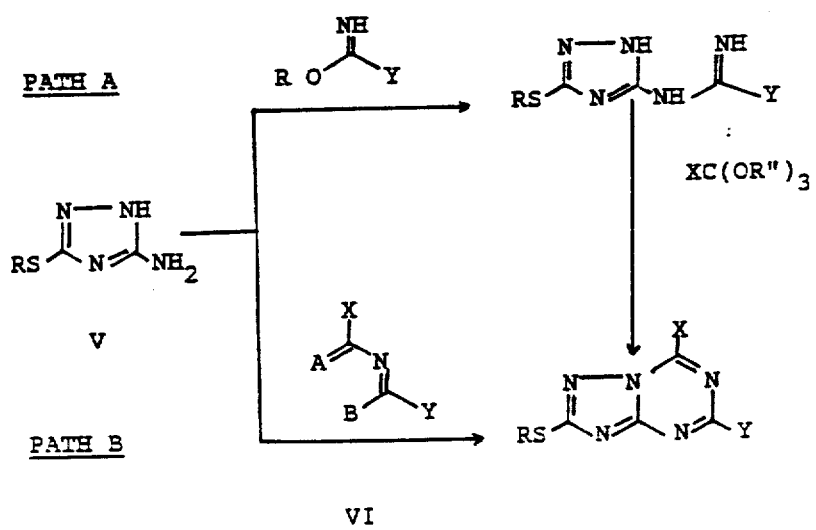

SCHEME III

A=O, S
B=OR', SR''', NR$_2$'''

III  R=H
IV   R=PhCH$_2$

UNITED STATES PATENT AND TRADEMARK OFFICE
CERTIFICATE OF CORRECTION

PATENT NO. : 4,605,433

DATED : August 12, 1986

INVENTOR(S) : Norman R. Pearson and William A. Kleschick

It is certified that error appears in the above-identified patent and that said Letters Patent is hereby corrected as shown below:

Column 6, between lines 29 and 43, SCHEME V,

"

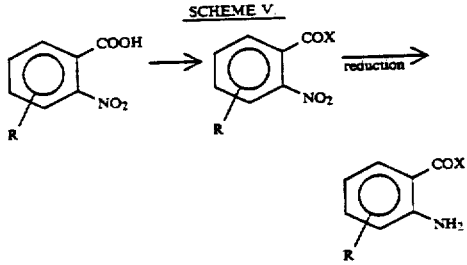

" should read

-- SCHEME V.

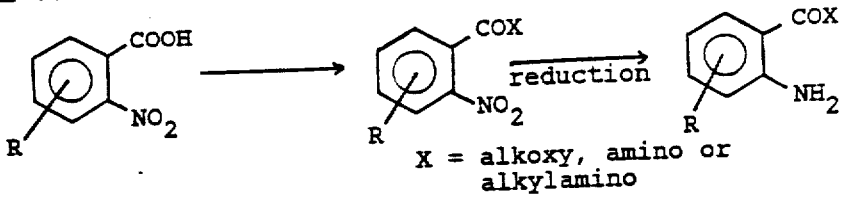

--.

UNITED STATES PATENT AND TRADEMARK OFFICE
CERTIFICATE OF CORRECTION

PATENT NO. : 4,605,433  Page 4 of 8
DATED : August 12, 1986
INVENTOR(S) : Norman R. Pearson and William A. Kleschick It is certified that error appears in the above-identified patent and that said Letters Patent is hereby corrected as shown below:

Column 6, between lines 51 and 66, SCHEME VI,

" 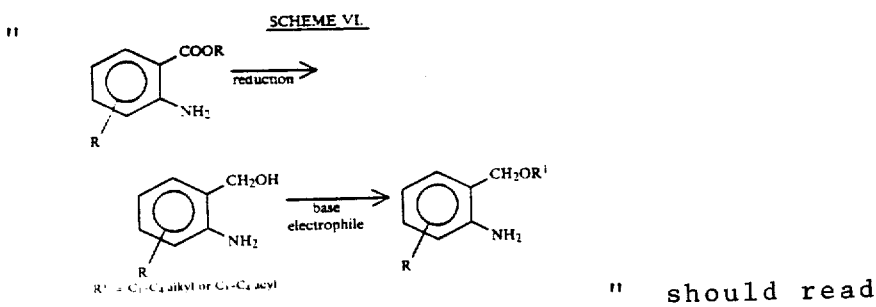  " should read

-- 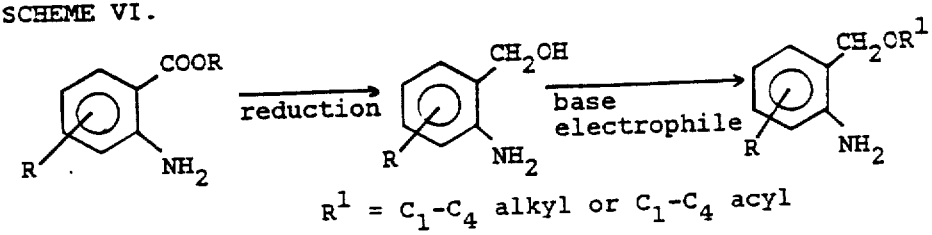 --.

UNITED STATES PATENT AND TRADEMARK OFFICE
CERTIFICATE OF CORRECTION

PATENT NO. : 4,605,433
DATED : August 12, 1986
INVENTOR(S) : Norman R. Pearson and William A. Kleschick It is certified that error appears in the above-identified patent and that said Letters Patent is hereby corrected as shown below:

Column 8, between lines 1 and 15, formula SCHEME VII,

"

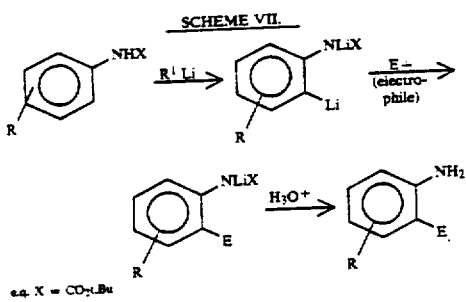

" should read

-- SCHEME VII.

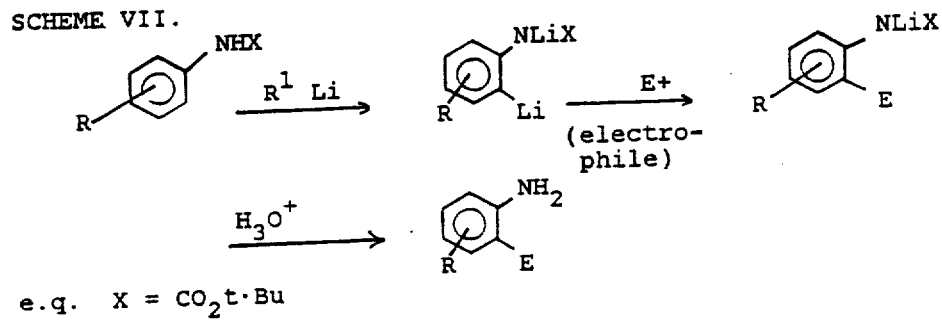

e.q. X = $CO_2$t·Bu

--.

UNITED STATES PATENT AND TRADEMARK OFFICE
CERTIFICATE OF CORRECTION

PATENT NO. : 4,605,433  Page 6 of 8
DATED : August 12, 1986
INVENTOR(S) : Norman R. Pearson and William A. Kleschick It is certified that error appears in the above-identified patent and that said Letters Patent is hereby corrected as shown below:

Column 8, between lines 25 and 35, formula Scheme VIII

"

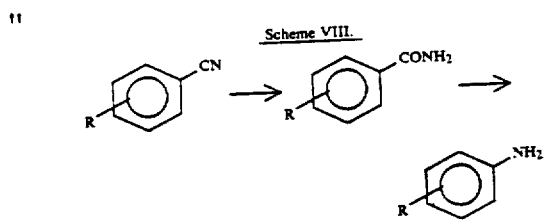

"  should read

-- Scheme VIII

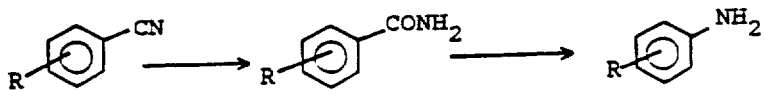

--.

UNITED STATES PATENT AND TRADEMARK OFFICE
CERTIFICATE OF CORRECTION

PATENT NO. : 4,605,433

DATED : August 12, 1986

INVENTOR(S) : Norman R. Pearson and William A. Kleschick

It is certified that error appears in the above-identified patent and that said Letters Patent is hereby corrected as shown below:

Column 15, line 4, "or" should read --of--.

Column 16, Claim 16, between lines 5 and 10, the first formula

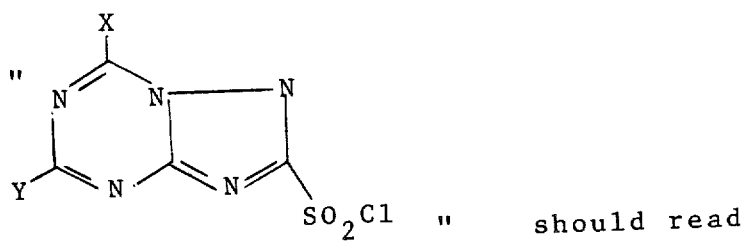   "   should read

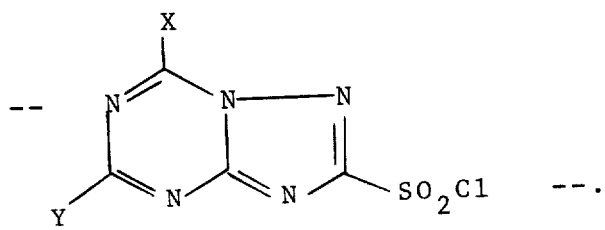   --.

UNITED STATES PATENT AND TRADEMARK OFFICE
CERTIFICATE OF CORRECTION

PATENT NO. : 4,605,433

DATED : August 12, 1986

INVENTOR(S) : Norman R. Pearson and William A. Kleschick

It is certified that error appears in the above-identified patent and that said Letters Patent is hereby corrected as shown below:

Column 16, line 34, delete, "alkylsulfonyl,".

Signed and Sealed this

Twenty-fifth Day of August, 1987

Attest:

DONALD J. QUIGG

Attesting Officer     Commissioner of Patents and Trademarks